United States Patent [19]

Gibbons

[11] 4,059,433

[45] Nov. 22, 1977

[54] 3-ALKOXYISOTHIAZOLE DERIVATIVES AS HERBICIDES

[75] Inventor: Loren Kenneth Gibbons, Medina, N.Y.

[73] Assignee: FMC Corporation, Philadelphia, Pa.

[21] Appl. No.: 697,457

[22] Filed: June 18, 1976

[51] Int. Cl.$^2$ .................... A01N 9/12; C07D 275/02
[52] U.S. Cl. ............................ 71/90; 260/306.8 A;
260/465.5 R; 260/465.7; 260/465.8 R
[58] Field of Search .................... 260/306.8 A; 71/90

[56] References Cited

U.S. PATENT DOCUMENTS 3,983,129  9/1976  Perronnet et al. ............ 260/306.8 A Primary Examiner—Richard J. Gallagher
Attorney, Agent, or Firm—Harrison H. Young, Jr.; Henry R. Ertelt

[57] ABSTRACT

A new class of herbicidal compounds consisting of 1-alkyl- and 1,1-dialkyl-3-(4-substituted-3-alkoxy-5-isothiazolyl)ureas and N-(4-substituted-3-alkoxy-5-isothiazolyl)alkanamides, in which the 4-substituent consists of alkoxycarbonyl, cyano and carbamoyl, exhibits preemergence and postemergence herbicidal activity, controlling effectively the growth of a wide spectrum of grassy and broad-leaved plant species. The synthesis of members of this class is described in detail, and the utility of representative compounds is exemplified.

14 Claims, No Drawings

3-ALKOXYISOTHIAZOLE DERIVATIVES AS HERBICIDES

This invention describes novel herbicidal compounds, new herbicidal compositions, and new methods for preventing and destroying undesired plant growth by preemergence and postemergence application of said new and useful herbicidal compositions to the locus where control is desired. Effective control of the growth of a variety of grassy and broad-leaved plant species is obtained. At herbicidally effective levels of application, some compounds of the invention show selectivity favorable to corn and related species. The herbicidal compositions may be applied and utilized by commonly accepted methods.

Herbicidal isothiazole compounds having an alkyl group on the 3-position of the isothiazole ring; a cyano, carboxamide or alkoxycarbonyl group on the 4-position; and a substituted urea on the 5-position have been described in the patent literature. See, for example, Belgian Pat. No. 817,903 and published French application No. 2,132,191. It has now been found that excellent herbicidal activity is obtained by having present on the 3-position, instead of an alkyl group, an alkoxy group. It has also been found that herbicidal activity is obtained with compounds having such a 3-alkoxy group, when the compound has in the 5-position, instead of a substituted urea group, a substituted alkanoylamino group. Thus, in one aspect of the invention, novel herbicidal compounds contain an isothiazole ring having the following classes of substituents: on the 3-position, an alkoxy group; on the 4-position, a cyano, carboxamide or alkoxycarbonyl group; and on the 5-position, a substituted urea or alkanoylamino group.

One group of herbicidal compounds in accordance with this invention has the following structure (on which the numbering of the various positions of the isothiazole ring is also indicated):

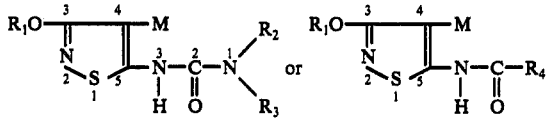

wherein $R_1$ is alkyl, alkenyl, cycloalkyl, $R_2$ is alkyl, cycloalkyl or methoxy, $R_3$ is alkyl or hydrogen, or $R_2$ and $R_3$ taken together form a divalent radical which may also contain a hetero atom, $R_4$ is alkyl, alkenyl, haloalkyl or haloalkenyl

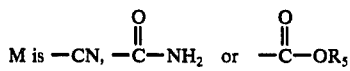

wherein $R_5$ is lower alkyl.

The alkyl, cycloalkyl, and alkenyl groups preferably have less than 10 carbon atoms; for $R_2$ and $R_3$ they preferably have less than 5 carbon atoms, while for $R_4$ they preferably have less than 7 carbon atoms. Examples of alkyl groups are methyl, ethyl, propyl, isopropyl, isobutyl, sec-butyl, tert-butyl, 2-pentyl, and so on. The divalent radicals formed by $R_2$ and $R_3$ preferably contain a total of four or five catenated atoms, no more than one of which is oxygen, sulfur or nitrogen. In the most preferred compounds, both $R_2$ and $R_4$ are alkyl of 1 to 4 carbons, $R_3$ is H and M is carboxamide.

Preparation of the compounds of the invention is described in the following examples. In the descriptions which follow, all temperatures are in degrees centigrade. All reduced pressures not otherwise designated are pressures normally attainable using a water aspirator.

EXAMPLE I

1-Methyl-3-(4-cyano-3-ethoxy-5-isothiazolyl)urea

A. Dibromomalononitrile - potassium bromide complex

A mixture of 99 g of malononitrile and 75 g of potassium bromide in 900 ml of water was cooled to 5°–10° and, while maintaining the temperature at 5°–10°, 488 g of bromine was added slowly during 2.75 hours. After addition was completed, the mixture was stirred for 2 hours at 5°–10°, and filtered. The collected solid was washed with 150 ml of ice-water and air-dried on the filter to give 356 g of the complex which was used without further purification.

B. Potassium tricyanomethanide

A mixture of 182.8 g of potassium cyanide and 1491 ml of 1,2-dimethoxyethane was stirred for 15 minutes at ambient temperature, then cooled to approximately 15°. Into the cold mixture was added, in small portions during 1 hour, 356 g of the dibromomalononitrile-potassium bromide complex from I. A. The mixture was stirred at ambient temperature for 2.5 hours, then heated to the reflux temperature. The hot solution was filtered through a steam-jacketed funnel and the filtrate was allowed to cool to ambient temperature. Diethyl ether (1750 ml) was added and the slurry was filtered. The solid was washed with cold ether and dried to give 152.5 g of potassium tricyanomethanide.

C. 3-Amino-3-ethoxy-2-cyano-2-propenenitrile

A mixture of 12.9 g of potassium tricyanomethanide from I B, 40 ml of water and 120 ml of diethyl ether was cooled to 5°. To this mixture was added 10 g of concentrated sulfuric acid dropwise at such a rate as to keep the reaction mixture temperature below 10°. Upon complete addition of sulfuric acid, the reaction mixture was stirred during 20 minutes. The mixture was then placed in a separatory funnel and the middle layer drawn off to be used in the next reaction. To 50 ml of the solution from above was added 150 ml of ethanol and volatile material was removed until the boiling temperature exceeded 50°, when the mixture was heated to reflux. The mixture was maintained at the reflux temperature for 15 hours. The white slurry was cooled to 10°, and the solid collected by filtration to give 6.5 g of 3-amino-3-ethoxy-2-cyano-2-propenenitrile, m.p. 233°. A small sample was recrystallized from ethanol without change of melting point. the nmr spectrum was consistent with the assigned structure.

D. 3-Amino-2-cyano-3-ethoxypropenethioamide

A mixture of 51.2 g of 3-amino-3-ethoxy-2-cyano-2-propenenitrile (above) and 37.8 g of triethylamine in 200 ml of pyridine was continuously stirred and heated to 70° while 60 g of gaseous hydrogen sulfide was bubbled in during 1.5 hours. Heating was continued at 65°–70° for 0.5 hour. Thin-layer chromatographic analysis indicated that no reaction had occurred. The mixture was heated overnight at 55° but still no reaction had occurred. An additional 150 ml of pyridine was added and the mixture was heated to 75°–80° while 17 g of hydrogen sulfide was bubbled in during 0.5 hour. Thin-layer chromatographic analysis indicated that a reaction had occurred, but was incomplete. An additional 18 g of hydrogen sulfide was added during 1 hour at 75°–80°; thin-layer chromatography indicated that the reaction was completed. The reaction mixture was evaporated to dryness under reduced pressure. The residue was recrystallized from ethanol to give a first crop of 28 g of 3-amino-2-cyano-3-ethoxypropenethioamide; m.p. 170°–171°. A second crop of 15 g of this product (m.p. 169°–171°) was obtained by diluting the mother liquor with ice-water. A small sample of crop I was recrystallized again from ethanol (charcoal) to give an analytical sample; m.p. 180°–181°. A total of 43.0 g of 3-amino-2-cyano-3-ethoxypropenethioamide was obtained. The nmr spectrum was consistent with the assigned structure.

Analysis: Calc'd for $C_6H_9N_3OS$: C, 42.11; H, 5.30; N, 24.55; S, 18.69; Found: C, 42.19; H, 5.46; N, 24.33; S, 18.55.

E. 5-Amino-4-cyano-3-ethoxyisothiazole

A mixture of 38 g of 3-amino-2-cyano-3-ethoxypropenethioamide (above) and 400 ml of ethanol was heated to the reflux temperature. To the hot mixture was added 26.0 ml of 30% hydrogen peroxide at a rate sufficient to maintain reflux. After addition was complete the reaction mixture was heated under reflux during one half hour. To the mixture was added 100 ml of ethanol, and reflux was continued during an additional one half hour, at which time thin-layer chromatography indicated that the reaction was complete. The reaction mixture was filtered hot. The filtrate was allowed to cool slowly overnight to give 26.0 g of 5-amino-4-cyano-3-ethoxyisothiazole; m.p. 216°–217°. The nmr spectrum was consistent with the assigned structure.

Analysis: Calc'd for $C_6H_7N_3OS$: C, 42.61; H, 4.17; N, 24.84; S, 18.92; Found: C, 42.81; H, 4.05; N, 24.88; S, 18.71.

F. 1-Methyl-3-(4-cyano-3-ethoxy-5-isothiazolyl)urea

A mixture of 10 g of 5-amino-4-cyano-3-ethoxyisothiazole (above), 3.7 g of methyl isocyanate and 20 drops of dibutyltin diacetate in 50 ml of tetrahydrofuran was heated under reflux for 17 hours, at which time thin-layer chromatography indicated reaction to be 15% complete. To the mixture was added 10 drops of dibutyltin diacetate and 3.7 g of methyl isocyanate; heating was continued for 48 hours; thin-layer chromatography indicated 70% reaction. An additional 10 drops of dibutyltin diacetate and 5 ml of methyl isocyanate was added and heating was continued for an additional 17 hours; at this time thin-layer chromatography indicated reaction to be complete. The reaction mixture was evaporated to dryness under reduced pressure and the brown solid was washed with pentane. Recrystallization from ethanol gave, after treatment with activated charcoal, 8.9 g of 1-methyl-3-(4-cyano-3-ethoxy-5-isothiazolyl)urea, m.p. 244°. The nmr and ir spectra were consistent with the assigned structure.

Analysis: Calc'd for $C_8H_{10}N_4O_2S$: C, 42.48; H, 4.46; N, 24.77; S, 14.15; Found: C, 42.42; H, 4.36; N, 24.76; S, 14.02.

EXAMPLE II

1-Methyl-3-(4-carbamoyl-3-ethoxy-5-isothiazolyl)urea

A solution of 5.6 g of 1-methyl-3-(4-cyano-3-ethoxy-5-isothiazolyl)urea (from Example I) in 10 ml of concentrated sulfuric acid was heated at 50° during 1.5 hours. The reaction mixture was poured into 200 ml of ice-water and stirred for one half hour. The resultant precipitate was collected by filtration and was allowed to air-dry overnight. The solid was slurried with 50 ml of saturated sodium bicarbonate solution. The resulting white solid was collected by filtration and recrystallized from ethanol to give 4.3 g of 1-methyl-3-(4-carbamoyl-3-ethoxy-5-isothiazolyl)urea, m.p. 240°–241°.

The nmr spectrum was consistent with the assigned structure.

Analysis: Calc'd for $C_8H_{12}N_4O_3S$: C, 39.35; H, 4.95; N, 22.99; S, 13.10; Found: C, 39.01; H, 5.15; N, 22.91; S, 13.17.

EXAMPLE III

1,1-Dimethyl-3-(4-cyano-3-ethoxy-5-isothiazolyl)urea

A. Phenyl (4-cyano-3-ethoxy-5-isothiazolyl)carbamate

A solution of 16.6 g of 5-amino-4-cyano-3-ethoxyisothiazole and 30.7 g of phenyl chloroformate in 100 ml of toluene under nitrogen atmosphere was stirred and heated at 100° for about 16 hours. After this time, thin-layer chromatography indicated that the reaction was 50% complete. An additional 15 ml of phenyl chloroformate was added and heating (100°) continued for an additional 24 hours; at this time thin-layer chromatography indicated 80% reaction. After an additional 6 hours, 90% reaction was indicated. The mixture was allowed to cool to 5° and filtered. The solid filter cake was washed with toluene and recrystallized from acetic acid, then ethanol, to give 11.5 g of phenyl (4-cyano-3-ethoxy-5-isothiazolyl)carbamate, m.p. 252°–253°. The nmr spectrum was consistent with the assigned structure.

Analysis: Calc'd for $C_{13}H_{11}N_3O_3S$: C, 53.98; H, 3.83; N, 14.53; S, 11.06; Found: C, 53.77; H, 3.97; N, 14.67; S, 11.27.

B. 1,1-Dimethyl-3-(4-cyano-3-ethoxy-5-isothiazolyl)urea

A solution of 9.5 g of phenyl (4-cyano-3-ethoxy-5-isothiazolyl)carbamate in 45 ml of dimethylformamide was placed in a pressure bottle; and while being stirred, was cooled below 0°. A total of 3.7 g of dimethylamine was collected in a dropping funnel by condensing the gas in a dry-ice trap. The liquified amine was added to the pressure bottle, and the bottle sealed. The contents of the bottle were allowed to warm to ambient temperature, then heated at 80° while being stirred overnight. The bottle was cooled to 5° and opened. The reaction mixture was evaporated to dryness under reduced pressure to give a brown solid. This solid was recrystallized from ethanol to give 5.9 g of 1,1-dimethyl-3-(4-cyano-3-ethoxy-5-isothiazolyl)urea, m.p. 204°–205°. The nmr spectrum was consistent with the assigned structure.

Analysis: Calc'd for: $C_9H_{12}N_4O_2S$: C, 45.00; H, 5.04; N, 23.32; S, 13.32; Found: C, 45.20; H, 5.22; N, 23.29; S, 12.97.

EXAMPLE IV

1,1-Dimethyl-3-(4-carbamoyl-3-ethoxy-5-isothiazolyl)urea

A mixture of 3.8 g of 1,1-dimethyl-3-(4-cyano-3-ethoxy-5-isothiazolyl)urea in 7 ml of concentrated sulfuric acid was treated as described in Example II to give 3.5 g of 1,1-dimethyl-3-(4-carbamoyl-3-ethoxy-5-isothiazolyl)urea, m.p. 172°–172°. The nmr spectrum was consistent with the assigned structure.

Analysis: Calc'd for $C_9H_{14}N_4O_3S$: C, 41.86; H, 5.46; N, 21.70; S, 12.39; Found: C, 42.02; H, 5.67; N, 21.90; S, 11.86.

EXAMPLE V

1-Methyl-3-(4-cyano-3-propoxy-5-isothiazolyl)urea

A. 3-Amino-2-cyano-3-propoxypropenenitrile

To a stirred mixture of 129.2 g of potassium tricyanomethanide (prepared as in Example I B), 600 g of propanol and 750 ml of dimethoxyethane was added dropwise 96.1 g of methanesulfonic acid, during 45 minutes. The exothermic reaction caused the reaction mixture temperature to rise slightly. The volatile materials were removed under reduced pressure and 800 ml of hot water was added to the residue. The solution was treated with charcoal and filtered. The filtrate was evaporated to dryness under reduced pressure. When the residue was allowed to stand at ambient temperature, the product crystallized. The mother liquor from above was diluted with two volumes of ice, to give additional product. The total yield of 3-amino-2-cyano-3-propoxypropenenitrile was 139 g.

B. 3-Amino-2-cyano-3-propoxypropenethioamide

A stirred mixture of 141 g of 3-amino-2-cyano-3-propoxypropenenitrile and 94.4 g of triethylamine in 250 ml of pyridine was heated at 80° for 4 hours while hydrogen sulfide gas was continually passed through the mixture. Thin-layer chromatography indicated reaction to be complete. The reaction mixture was diluted to 2 liters with water and the pale yellow precipitate was collected by filtration. The precipitate was recrystallized from ethanol to give 114 g of 3-amino-2-cyano-3-propoxypropenethioamide, m.p. 174°.

Analysis: Calc'd for $C_7H_{11}N_2OS$: C, 45.39; H, 5.99; N, 22.68; S, 17.31; Found: C, 45.19; H, 5.87; N, 22.66; S, 17.55.

C. 5-Amino-4-cyano-3-propoxyisothiazole

A mixture of 111 g of 3-amino-2-cyano-3-propoxypropene-thioamide in 250 ml of ethanol was heated to reflux. To this stirred mixture was added 20.4 g of 30% hydrogen peroxide, at such a rate as to maintain a uniform rate of reflux. After complete addition, the reaction mixture was heated under reflux for 20 minutes. A quantity of activated charcoal was added to the reaction mixture. The reaction mixture was filtered hot and allowed to cool. The filtrate was poured into 1500 ml of water, and the solid precipitate was collected by filtration. The dried solid was recrystallized from toluene, to give 104.5 g of 5-amino-4-cyano-3-propoxyisothiazole, m.p. 122°–125°.

The nmr and ir spectra were consistent with the assigned structure.

Analysis: Calc'd for $C_7H_9N_3OS$: C, 45.89; H, 4.95; N, 22.93; S, 17.50; Found: C, 46.02; H, 5.10; N, 22.66; S, 17.32.

D. 1-Methyl-3-(4-cyano-3-propoxy-5-isothiazolyl)urea

A mixture of 11 g of 5-amino-4-cyano-3-propoxythiazole, 6.8 g of methyl isocyanate and 2 ml of dibutyltin diacetate in 50 ml of tetrahydrofuran was heated under reflux. Thin-layer chromatography indicated the reaction was complete after 4 hours. The reaction mixture was evaporated to dryness under reduced pressure. The residue was recrystallized from ethanol to give, in two crops, 12.5 g of 1-methyl-3-(4-cyano-3-propoxy-5-isothiazolyl)urea, m.p. 220° (decomposes). The nmr and the ir spectra were consistent with the assigned structure.

Analysis: Calc'd for $C_9H_{12}N_4O_2S$: C, 44.99; H, 5.04; N, 23.32; S, 13.34; Found: C, 44.96; H, 4.92; N, 23.30; S, 13.28.

EXAMPLE VI

1-Methyl-3-(4-carbamoyl-3-propoxy-5-isothiazolyl)urea

A mixture of 8.5 g of 1-methyl-3-(4-cyano-3-propoxy-5-isothiazolyl)urea with 20 ml of concentrated sulfuric acid was heated to 50° during 1 hour. Analysis by thin-layer chromatography at this time indicated the reaction to be complete. The reaction mixture was poured with stirring into 200 ml of water. The resulting solution was neutralized with ammonium hydroxide solution and the precipitate was collected by filtration. The dried solid was recrystallized from ethanol to give 6.3 g of 1-methyl-3-(4-carbamoyl-3-propoxy-5-isothiazolyl)urea, m.p. 195°–198°. The nmr and ir spectra were consistent with the assigned structure.

Analysis: Calc'd for $C_9H_{14}N_4O_3S$: C, 41.85; H, 5.46; N, 21.69; S, 12.41; Found: C, 41.86; H, 5.20; N, 21.52; S, 12.26.

EXAMPLE VII

N-(4-Cyano-3-propoxy-5-isothiazolyl)-2-methylpropanamide

A mixture of 11 g of 5-amino-4-cyano-3-propoxyisothiazole (prepared as in V C), and 19 grams of isobutyric anhydride was heated to approximately 80° and a catalytic amount of gaseous hydrogen chloride was added. The gas addition resulted in an exothermic reaction. The reaction mixture was heated at 100° for 3–4 hours and then evaporated to dryness under reduced pressure. The residue was recrystallized from ethanol in the presence of activated charcoal, to give 12.6 g of N-(4-cyano-3-propoxy-5-isothiazolyl)-2-methylpropanamide, m.p. 220°–221°. The nmr and ir spectra were consistent with the assigned structure.

Analysis: Calc'd for $C_{11}H_{15}N_3O_2S$: C, 52.16; H, 5.96; N, 16.59; S, 12.66; Found: C, 52.20; H, 6.17; N, 16.43; S, 12.71.

EXAMPLE VIII

N-(4-Carbamoyl-3-propoxy-5-isothiazolyl)-2-methylpropanamide

A mixture of 8.6 g of N-(4-cyano-3-propoxy-5-isothiazolyl)-2-methylpropanamide, from Example VII, in 20 ml of concentrated sulfuric acid was heated at 50° for 1 hour. Thin-layer chromatographic analysis indicated that the reaction was complete. The reaction mixture was poured into 200 ml of cold water. The solution was neutralized with ammonium hydroxide. The resulting precipitate was collected by filtration. The dried solid was recrystallized from toluene to give 7.7 g of N-(4-carbamoyl-3-propoxy-5-isothiazolyl)-2-methylpropanamide m.p. 153°–154°. The nmr and ir spectra were consistent with the assigned structure.

Analysis: Calc'd for $C_{11}H_{17}N_3O_3S$: C, 48.69; H, 6.32; N, 15.49; S, 11.82; Found: C, 48.89; H, 6.46; N, 15.69; S, 11.89.

EXAMPLE IX

1-Methyl-3-(3-ethoxy-4-ethoxycarbonyl-5-isothiazolyl)urea

A. Ethyl 3-amino-3-ethoxyacrylate

In an oven-dried flask were placed 113.1 g of redistilled ethyl cyanoacetate, 46 g of ethanol (distilled from calcium hydride), and 500 ml of anhydrous diethyl ether. The solution was cooled to 0°, 36.5 g of hydrogen chloride gas were added and the flask was sealed. The mixture was refrigerated for several days until precipitation of white solid was observed. The white precipitate was collected by filtration and immediately resuspended in approximately 300 ml of diethyl ether. The ether-suspension was mixed with 1000 ml of a 40% aqueous solution of potassium carbonate (previously cooled to 0°). The ether layer was separated and placed over 30 g of anhydrous potassium carbonate. The aqueous phase was washed three times with 150 ml portions of diethyl ether. The washings were added to the ether phase over potassium carbonate. The combined ether phase and washings were decanted onto approximately 80 g of fresh anhydrous potassium carbonate. The potassium carbonate was removed by filtration and the ether was removed by evaporation under reduced pressure. The residue was distilled at 0.25 mm hg. The fraction distilling at 60° was collected to yield 85.5 g of ethyl 3-amino-3-ethoxyacrylate, $n_D^{25}$ = 1.4808. The ir and nmr spectra were consistent with the assigned structure.

Analysis: Calc'd for $C_7H_{13}NO_3$: C, 52.82; H, 8.23; N, 8.80; Found: C, 52.55; H, 8.50; N, 8.90.

B. Phenyl (3-ethoxy-4-ethoxycarbonyl-5-isothiazolyl)carbamate

A mixture of 66.1 g of ethyl 3-amino-3-ethoxyacrylate and 300 ml of diethyl ether was stirred in a 500 ml flask during the addition of 60.5 g of phenoxycarbonylisothiocyanate. A solution of 38.3 ml of 33% hydrogen peroxide (11.5 g of active $H_2O_2$) in 300 ml of ethanol was added to the reaction mixture at a rate sufficient to maintain uniform reflux. The reaction mixture was allowed to stand at ambient temperature over a weekend. The precipitate was collected by filtration and dried. The filter cake was recrystallized from 1400 ml of 1:1 acetonitrile:water to yield 44.1 g of phenyl (3-ethoxy-4-ethoxycarbonyl-5-isothiazolyl)carbamate, mp 130° (decomposes). The ir spectrum was consistent with the assigned structure.

C. 1-Methyl-3-(3-ethoxy-4-ethoxycarbonyl-5-isothiazolyl)urea

In the manner of Example III B, 8.4 g of phenyl (3-ethoxy-4-ethoxycarbonyl-5-isothiazolyl)carbamate in 20 ml of dimethylformamide was treated with 1.6 g of methylamine. The solid from the reaction mixture was collected by filtration and dried to yield material melting at 188°–190°. Recrystallization from ethanol gave material melting at 188°–191°. A second recrystallization from benzene gave 3.7 g of 1-methyl-3-(3-ethoxy-4-ethoxycarbonyl-5-isothiazolyl)urea, m.p. 195°–196°. The ir and nmr spectra were consistent with the assigned structure.

Analysis calc'd for $C_{10}H_{15}N_3O_4S$: C, 43.95; H, 5.53; N, 15.37; S, 11.73; O, 23.42; Found: C, 43.97; H, 5.45; N, 15.62; S, 11.60.

EXAMPLE X 1,1-Dimethyl-3-(3-ethoxy-4-ethoxycarbonyl-5-isothiazolyl)urea

In the manner of Example II B, 8.4 g of phenyl (3-ethoxy-4-ethoxycarbonyl-5-isothiazolyl)carbamate in 20 ml of dimethylformamide were treated with 2.3 g of dimethylamine. The solid from the reaction mixture was recrystallized from ethanol to yield 1.9 g of 1,1-dimethyl-3-(3-ethoxy-4-ethoxycarbonyl-5-isothiazolyl)urea, mp 164°–165°. The ir and nmr spectra were consistent with the assigned structure.

Analysis calc'd for $C_{11}H_{17}N_3O_4S$: C, 45.98; H, 5.96; N, 14.62; S, 11.16; O, 22.27; Found: C, 46.22; H, 6.18; N, 14.38; S, 11.41; O, 21.81.

EXAMPLE XI 1,1-Diethyl-3-(3-ethoxy-4-ethoxy-carbonyl-5-isothiazolyl)urea

In the manner of Example II B, 8.4 g of phenyl (3-ethoxy-4-ethoxycarbonyl-5-isothiazolyl)carbamate in 20 ml of dimethylformamide were allowed to react with 3.7 g of diethylamine. The solid from the reaction mixture was recrystallized from ethanol:water (70:30) to give 3.2 g of 1,1-diethyl-3-(3-ethoxy-4-ethoxycarbonyl-5-isothiazolyl)urea, m.p. 77°–80°. The nmr spectrum was consistent with the assigned structure.

Analysis: Calc'd for $C_{13}H_{21}N_3O_4S$: C, 49.51; H, 6.71; N, 13.32; S, 10.17; Found: C, 49.54; H, 6.43; N, 13.61; S, 10.32.

EXAMPLE XII

1-Methyl-3-(4-cyano-3-isopropoxy-5-isothiazolyl)urea

A. 3-Amino-2-cyano-3-isopropoxy-2-propenenitrile

In the manner of Example V A, 129.2 g of potassium tricyanomethanide and 1000 ml of isopropanol were treated with 65 ml (96 g) of methanesulfonic acid to yield 104 g of 3-amino-2-cyano-3-isopropoxy-2-propenenitrile, which was used as an intermediate without further purification. The ir spectrum was consistent with the assigned structure.

In two previous small scale runs an additional 14 g of the nitrile had been prepared. The combined products were used in the subsequent preparation of the thioamide intermediate.

B. 3-Amino-2-cyano-3-isopropoxy-2-propenethioamide

In the manner of Example V, part B, 117.6 g of 3-amino-2-cyano-3-isopropoxy-2-propenenitrile were allowed to react with excess hydrogen sulfide gas in a solution of 157.4 g of triethylamine and 250 ml of pyridine. The volatile materials were removed under reduced pressure and water was added to the residue. The yellow precipitate was collected and dried. The dried solid was recrystallized from isopropanol to yield 123 g of 3-amino-2-cyano-3-isopropoxy-2-propenethioamide, mp 170° (decomposes). The ir and nmr spectra were consistent with the assigned structure.

Analysis: Calc'd for $C_7H_{11}N_3SO$: C, 45.39; H, 5.99; N, 22.68; S, 17.31; Found: C, 45.68; H, 5.90; N, 22.78; S, 17.50.

C. 5-Amino-4-cyano-3-isopropoxyisothiazole

In the manner of Example V C, 123 g of 3-amino-2-cyano-3-isopropoxy-2-propenethioamide in 500 ml of isopropanol were treated with 80 ml of 30% hydrogen peroxide (22.6 g of active $H_2O_2$). The residue from the reaction was recrystallized from toluene to yield 108.4 g of 5-amino-4-cyano-3-isopropoxyisothiazole, mp 146°–148°. The nmr and ir spectra were consistent with the assigned structure.

D. 1-Methyl-3-(4-cyano-3-isopropoxy-5-isothiazolyl)urea

In the manner of Example V D, a mixture of 11 g of 5-amino-4-cyano-3-isopropoxyisothiazole and 6.8 g of methyl isocyanate in 50 ml of dry tetrahydrofuran containing 2 ml of dibutyltin diacetate were allowed to react under reflux overnight. Volatile materials were removed under reduced pressure and the residue was recrystallized from ethyl acetate to yield 10.8 g of 1-methyl-3-(4-cyano-3-isopropoxy-5-isothiazolyl)urea, mp 238° (decomposes.) The ir and nmr spectra were consistent with the assigned structure.

Analysis: Calc'd for $C_9H_{12}N_4SO_2$: C, 44.09; H, 5.04; N, 23.32; S, 13.34; Found: C, 45.09; H, 5.04; N, 23.06; S, 13.13.

EXAMPLE XIII

N-(4-Cyano-3-isopropoxy-5-isothiazolyl)-2-methylpropanamide

In the manner of Example VII, 11 g of 5-amino-4-cyano-3-isopropoxyisothiazole (prepared in Example XII C) and 19 g of isobutyric anhydride were treated with a catalytic amount of hydrogen chloride gas. The solidified reaction mixture was mixed with 200 ml of a 1:1 mixture of ethanol and saturated aqueous sodium bicarbonate solution and filtered. The residue was recrystallized from ethyl acetate to yield 11.3 g of N-(4-cyano-3-isopropoxy-5-isothiazolyl)-2-methylpropanamide, mp 224°. The ir and nmr spectra were consistent with the assigned structure.

Analysis calc'd for: $C_{11}H_{15}N_3O_2S$: C, 52.16; N, 16.59; S, 12.66; O, 12.63; Found: C, 52.24; H, 6.07; N, 16.68; S, 12.60.

The herbicidal activities of the compounds of this invention were demonstrated as follows. In preemergence tests, rows of seeds of lima beans (*Phaseolus lunatus*), corn (*Zea mays*), wild oats (*Avena fatua*), lettuce (*Lactuca sativa*), mustard (*Brassica Juncea*) and crabgrass (*Digitaria sanguinalis*) were planted in shallow flat-bed trays (20cm × 15cm × 7.5cm) containing 5cm to 7.5cm of sandy loam soil. Within 24 hours after planting, an aqueous acetone solution of the compound (using sufficient acetone to obtain solution) was sprayed on the soil at a rate equivalent to 8.96 kilograms per hectare, using a total volume equivalent to 760 liters per hectare. The trays were maintained under normal growing conditions in the greenhouse for about 3 weeks, after which the herbicidal efficacy of the compound was assessed. Individual plant species were examined in comparison with untreated plants. Table 1 lists data collected in preemergence tests with compounds of the present invention.

In postemergence tests, rows of seeds were planted as for preemergence tests and the untreated flats were maintained in the greenhouse until the first trifoliate leaves of the bean plants were unfolding. The test plants were then sprayed with an aqueous acetone solution of the compound as for preemergence tests. The plants were returned to the greenhouse and held under normal growing conditions for about 3 more weeks, after which the herbicidal efficacy of the compound was assessed. Table 2 lists data collected in postemergence tests with compounds of the present invention.

Table 1

| Preemergence Herbicidal Activity of 3-Alkoxyisothiazolylureas and -alkanamides (expressed as % kill at 8.96 kg/hectare) | | | | | | |
|---|---|---|---|---|---|---|
| Compound of example | Lima Bean | Corn | Wild Oats | Lettuce | Mustard | Crabgrass |
| I | 100 | 0 | 40 | 100 | 100 | 80 |
| II | 100 | 100 | 100 | 100 | 100 | 100 |
| III | 100 | 0 | 80 | 100 | 100 | 30 |
| IV | 100 | 100 | 100 | 100 | 100 | 100 |
| V | 100 | 0 | 20 | 30 | 100 | 40 |
| VI | 100 | 100 | 100 | 100 | 100 | 100 |
| VII | 0 | 0 | 0 | 0 | 0 | 0 |
| VIII | 100 | 30 | 30 | 100 | 100 | 100 |
| IX | 0 | 0 | 50 | 70 | 80 | 50 |
| X | 0 | 0 | 0 | 0 | 0 | 0 |
| XI | 0 | 0 | 0 | 0 | 100 | 0 |
| XII | 100 | 0 | 70 | 100 | 100 | 100 |
| XIII | 0 | 0 | 0 | 0 | 90 | 0 |

Table 2

| Postemergence Herbicidal Activity of 3-Alkoxyisothiazolylureas and -alkanamides (expressed as % kill at 8.96 kg/hectare) | | | | | | |
|---|---|---|---|---|---|---|
| Compound of example | Lima Bean | Corn | Wild Oats | Lettuce | Mustard | Crabgrass |
| I | 75 | 0 | 40 | 100 | 100 | 100 |
| II | 100 | 100 | 100 | 100 | 100 | 100 |
| III | 100 | 0 | 60 | 100 | 100 | 30 |
| IV | 100 | 100 | 100 | 100 | 100 | 100 |
| V | 100 | 0 | 30 | 100 | 100 | 30 |
| VI | 100 | 100 | 100 | 100 | 100 | 100 |
| VII | 0 | 0 | 0 | 0 | 0 | 50 |
| VIII | 30 | 0 | 30 | 100 | 100 | 100 |
| IX | 0 | 0 | 30 | 100 | 100 | 30 |
| X | 0 | 0 | 0 | 30 | 40 | 0 |
| XI | 0 | 0 | 0 | 100 | 75 | 0 |
| XII | 100 | 0 | 100 | 100 | 100 | 100 |
| XIII | 50 | 0 | 0 | 50 | 50 | 20 |

For herbicidal application, the compounds of this invention may be utilized in diverse formulations including the agricultural adjuvants and agricultural carriers, i.e. those materials normally employed to facilitate the dispersion of active ingredients in agricultural applications, recognizing the fact that the formulation and mode of application of a toxicant may affect the activity of the material in a given application. Thus, a compound of this invention may be formulated as a granule of relatively large particle size, as a wettable powder, as an emulsifiable concentrate, as a solution, or as any of several other known types of formulations, depending on the desired mode of application.

Granular formulations are particularly useful for aerial distribution or for penetration of a canopy of foilage. Useful granular formulations may be of several types. Impregnated granules are those wherein the active ingredient is applied to large particles of an absorbent carrier, such as an attapulgite or kaolin clay, corncobs, expanded mica, etc., normally in the form of a solution in a solvent. Surface-coated granules may be produced by spraying the molten active ingredient onto the surface of a generally nonabsorbent particle or by spraying on a solution of active ingredient in a solvent. The core may be water-soluble such as a prilled fertilizer, or insoluble such as sand, marble chips or coarse talc. Particularly useful is a granule wherein a wettable powder is applied as a surface coating to a sand or other insoluble particle such that the wettable powder may be dispersed on contact of the granule with moisture. Granules may be produced by agglomeration of dusts or powders by compaction rollers, by extrusion through a die or by use of a granulating disc. Granular formulations may vary widely in concentration, with useful formulations containing as little as 0.5% or as much as 95% of active ingredient.

Wettable powders, also useful formulations for both pre- and postemergence herbicides, are in the form of finely divided particles which disperse readily in water or other dispersants. The wettable powder is ultimately applied to the soil or to the undesired plant growth either as a finely divided dry material or as an emulsion in water or other liquid. Typical carriers for wettable powders include fuller's earth, kaolin clays, silicas and other highly absorbent, readily wet inorganic diluents. Wettable powders normally are prepared to contain about 5% to 80% of active ingredient, depending on the absorbency of the carrier, and usually also contain a small amount of a wetting, dispersing or emulsifying agent to facilitate dispersion. For example, a useful wettable powder formulation contains 80.8 parts of 1-methyl-3-(4-carbamoyl-3-ethoxy-5-isothiazolyl)urea, 17.9 parts of palmetto clay, and 1.0 part of sodium lignosulfonate and 0.3 part of sulfonated aliphatic polyester as wetting agents.

Other useful formulations for herbicidal applications are the emulsifiable concentrates, which are homogeneous liquid or paste compositions dispersible in water or other dispersant, and may consist entirely of a compound of this invention with a liquid or solid emulsifying agent, or may also contain an agriculturally acceptable liquid carrier, such as xylene, heavy aromatic naphthas, isophorone and other nonvolatile organic solvents.

Typical wetting, dispersing or emulsifying agents used in agricultural formulations include, for example, the alkyl and alkylaryl sulfonates and sulfates and their sodium salts; polyethylene oxides; sulfonated oils, fatty acid esters of polyhydric alcohols; and other types of surface-active agents, many of which are available in commerce. The surface-active agent, when used, normally comprises from 1% to 15% by weight of the herbicidal composition.

These formulations may be applied without further dilution or as dilute solutions, emulsions or suspensions in water or other suitable diluent. The compositions may be applied to the area wherein control is desired by spraying onto the undesired vegetation or onto the surface of the soil in the case of liquid compositions or by distribution from mechanical equipment in the case of solids. The surface-applied material may also be blended into the upper layer of soil by cultivation, or left as applied, as is appropriate to gain the optimum results with the particular treatment.

The active herbicidal compounds of this invention may be formulated and/or applied with insecticides, fungicides, nematicides, plant-growth regulators, fertilizers, and other agricultural chemicals. In applying the active compounds of this invention, whether formulated alone or with other agricultural chemicals, an effective amount and concentration of isothiazolylurea are of course employed.

It is apparent that various modifications may be made in the formulation and application of the novel compounds of this invention, without departing from the inventive concept herein, as defined in the following claims:

I claim:

1. A substituted isothiazolylurea of the formula:

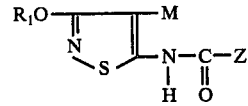

in which $R_1$ is alkyl of 1–5 carbon atoms; M is cyano or carbamoyl; Z is $-NR_2R_3$ or $R_4$, wherein $R_2$ is alkyl of 1–5 carbon atoms, $R_3$ is alkyl of 1–5 carbon atoms or hydrogen, $R_4$ is alkyl of 1–5 carbon atoms.

2. A compound of claim 1 in which Z is $-NR_2R_3$.

3. A compound of claim 2 in which M is cyano.

4. The compound of claim 3 which is 1-methyl-3-(4-cyano-3-ethoxy-5-isothiazolyl)urea.

5. The compound of claim 3 which is 1,1-dimethyl-3-(4-cyano-3-ethoxy-5-isothiazolyl)urea.

6. The compound of claim 3 which is 1-methyl-3-(4-cyano-3-isopropoxy-5-isothiazolyl)urea.

7. A compound of claim 2 in which M is carbamoyl.

8. The compound of claim 7 which is 1-methyl-3-(4-carbamoyl-3-ethoxy-5-isothiazolyl)urea.

9. The compound of claim 7 which is 1,1-dimethyl-3-(4-carbamoyl-3-ethoxy-5-isothiazolyl)urea.

10. The compound of claim 7 which is 1-methyl-3-(4-carbamoyl-3-propoxy-5-isothiazolyl)urea.

11. A compound of claim 1 in which Z is $R_4$.

12. The compound of claim 11 which is N-(4-carbamoyl-3-propoxy-5-isothiazolyl)-2-methylpropanamide.

13. An herbicidal composition comprising an herbicidally effective amount of a compound of claim 1 in admixture with an extruder.

14. A method of preventing and destroying undesired plant growth which comprises applying to the locus to be protected an herbicidally effective amount of a compound of claim 1.

* * * * *

UNITED STATES PATENT AND TRADEMARK OFFICE
CERTIFICATE OF CORRECTION

PATENT NO. : 4,059,433
DATED : November 22, 1977
INVENTOR(S) : L. K. Gibbons

It is certified that error appears in the above—identified patent and that said Letters Patent is hereby corrected as shown below:

Column 2, line 57, "the nmr spectrum" should read --The nmr spectrum--. Column 5, line 10, "172°-172°." should read --172°-173°.--. Column 9, line 30, "C, 44.09; H,5.04;" should read --C 44.99; H 5.04;--; line 49, "C,52.16; N, 16.59;" should read --C 52.16; H 5.97; N 16.59;--. Column 12, line 52, "extruder." should read --extender.--.

Signed and Sealed this

Eighteenth Day of November 1980

[SEAL]

Attest:

SIDNEY A. DIAMOND

Attesting Officer

Commissioner of Patents and Trademarks